United States Patent
Holmstrom et al.

(10) Patent No.: US 8,781,579 B2
(45) Date of Patent: Jul. 15, 2014

(54) IMPLANTABLE MEDICAL DEVICE FOR CARDIAC THERAPY

(75) Inventors: Nils Holmstrom, Jarfalla (SE); John Gustafsson, Hagersten (SE); Michael Broome, Ekero (SE)

(73) Assignee: St. Jude Medical AB, Jarfalla (SE)

( * ) Notice: Subject to any disclaimer, the term of this patent is extended or adjusted under 35 U.S.C. 154(b) by 126 days.

(21) Appl. No.: 13/510,873

(22) PCT Filed: Dec. 8, 2009

(86) PCT No.: PCT/EP2009/066647
§ 371 (c)(1), (2), (4) Date: May 18, 2012

(87) PCT Pub. No.: WO2011/069538
PCT Pub. Date: Jun. 16, 2011

(65) Prior Publication Data
US 2012/0239102 A1    Sep. 20, 2012

(51) Int. Cl.
*A61N 1/368* (2006.01)
*A61N 1/362* (2006.01)
*A61N 1/05* (2006.01)

(52) U.S. Cl.
CPC .............. *A61N 1/368* (2013.01); *A61N 1/3684* (2013.01); *A61N 2001/0585* (2013.01); *A61N 1/3627* (2013.01)
USPC ................................................ 607/9; 607/15

(58) Field of Classification Search
CPC ... A61N 1/056; A61N 1/0563; A61N 1/3622; A61N 1/362; A61N 1/368; A61N 1/3684; A61N 1/3752
USPC .................................. 607/9, 11, 15
See application file for complete search history.

(56) References Cited

U.S. PATENT DOCUMENTS

| | | | |
|---|---|---|---|
| 6,909,916 B2 * | 6/2005 | Spinelli et al. | 607/9 |
| 2002/0143368 A1 * | 10/2002 | Bakels et al. | 607/9 |
| 2002/0169484 A1 | 11/2002 | Mathis et al. | |
| 2003/0120316 A1 | 6/2003 | Spinelli et al. | |
| 2004/0106958 A1 | 6/2004 | Mathis | |
| 2005/0125041 A1 * | 6/2005 | Min et al. | 607/9 |
| 2006/0020294 A1 | 1/2006 | Brockway et al. | |
| 2009/0306732 A1 | 12/2009 | Rosenberg et al. | |

FOREIGN PATENT DOCUMENTS

WO        2005039690 A1    5/2005

OTHER PUBLICATIONS

International Search Report—Int'l App. No. PCT/EP2009/066647; Int'l Filing Date: Dec. 8, 2009.
Written Opinion of the Int'l Searching Authority—Int'l App. No. PCT/EP2009/066647; Int'l Filing Date: Dec. 8, 2009.
Buckberg, Gerald MD et al., "Cardiac Mechanics Revisited—The Relationship of Cardiac Architecture to Ventricular Function," Circulation. 2008;118:2571-2587.

* cited by examiner

*Primary Examiner* — Allen Porter, Jr.

(57) ABSTRACT

An implantable medical device, IMD, (100) is connectable to at least one ventricular lead (210) having a ventricular basal electrode (214) and a ventricular apical electrode (212). The IMD (100) comprises a pulse generator (120) for generating pacing pulses applied to a heart (10) through the ventricular lead (210). The operation of this pulse generator (120) is controlled by a controller (130) that is configured to control the pulse generator to first deliver a pacing pulse to the ventricular basal electrode (214) to stimulate the basal portion of the ventricle (12, 14) before a pacing pulse is delivered to the apical portion of the ventricle (12, 14) by the ventricular apical electrode (212). This pulse sequence achieves a biologically more correct cardiac stimulation and a contraction pattern that reduces the risk for valvular regurgitation.

15 Claims, 8 Drawing Sheets

IMPLANTABLE MEDICAL DEVICE FOR CARDIAC THERAPY

TECHNICAL FIELD

The present invention generally relates to implantable medical devices, and in particular to such implantable medical devices adapted for applying cardiac therapy.

BACKGROUND

Heart failure is an increasing health problem worldwide. Five million people in the United States and 15 million people among the 900 million people represented by the European Society of Cardiology (ESC) are suffering from heart failure. A similar number of people have asymptomatic cardiac dysfunction.

Heart failure conditions may be characterized by weakness, breathlessness, abdominal discomfort, edema in the lungs and the lower portions of the body. These symptoms are associated with the inability of the heart to pump sufficient amounts of blood without unduly raising filling pressures. Insufficiency may be associated with either the left ventricle, the right ventricle, or both. Heart failure may be caused by inefficient contractions caused by a disturbed physiologic conduction system. This disturbance may be caused by, for instance, ischemia, infarction, fibrosis or dilatation.

A possible approach of treating patients suffering from various heart failure conditions is to use an implantable medical device, such as a pacemaker, providing cardiac pacing to the failing heart. For instance, cardiac pacing to resynchronize ventricular contractions has been shown to increase cardiac output and has been observed to produce reverse cardiac remodelling in human clinical studies.

Cardiac pacing can be achieved by applying a pacing pulse to a selected portion of the heart, in particular to the ventricles of the heart. In the art, such a pacing pulse has been applied at or close to the apex of the ventricles to cause propagation of a depolarization wave towards the base of the ventricles to start the contraction of the ventricles close to the heart apex and then move the contractile pattern towards the semilunar valves. It is believed that such a pacing and resulting contractive pattern will efficiently empty the blood present in the ventricles through the aortic valve and the pulmonary valve and into the aorta and the pulmonary artery, respectively.

The traditional apex-to-base stimulation approach is, though, different from the true cardiac motion occurring following intrinsic depolarization during a cardiac cycle. In particular, apex-to-base stimulation may have an increased risk of mitral regurgitation during systolic emptying of the ventricles.

US 2004/0106958 discloses an implantable medical device connected to a multi-electrode lead positioned in the right ventricle and designed to treat congestive heart failure. An electrode mapping procedure is conducted in order to identify optimal stimulating electrode of the multiple electrodes on the lead. The mapping procedure can be conducted in order to find a suitable stimulating electrode near the right ventricular outflow tract to reduce mitral regurgitation.

The U.S. patent application can thereby be used to reduce the risk of mitral regurgitation but still has limitations in terms of not achieving optimal cardiac movement during systolic pacing of the heart.

*Circulation Cardiovascular Imaging* 2009, 2: 444-450 discloses that mitral regurgitation in heart failure patients can be reduced with cardiac resynchronization therapy (CRT). It was concluded that reduction in functional mitral regurgitation after CRT is associated with improved left ventricular closing pressures on the mitral valve. CRT results in more sustained peak closing pressures on the mitral valve during systole as demonstrated by a higher closing pressure ratio after CRT due to improved left ventricular contractility and/or improved coordination of left ventricular contraction.

Although reducing the problems associated with mitral regurgitation, the proposed CRT therapy does still not achieve optimal cardiac movement during systolic pacing of the heart.

SUMMARY

Embodiments are directed towards solving or at least mitigating this and other problems of the prior art techniques.

It is a general objective to provide an implantable medical device capable of delivering stimulating pacing therapy to achieve biologically relevant cardiac motion.

It is a particular objective to provide an implantable medical device capable of delivering stimulating pacing therapy that reduces the risk of mitral regurgitation.

These and other objectives are met by embodiments as disclosed herein.

Briefly, an implantable medical device designed for delivering cardiac therapy comprises a lead connector connectable to at least one cardiac lead. The cardiac lead comprises a ventricular apical electrode and a ventricular basal electrode.

The IMD also comprises a pulse generator connected to the lead connector and configured to generate a sequence of pacing pulses during a cardiac cycle. The pulse generator is controlled by a controller implemented in the IMD. The controller is configured to control the pulse generator to first generate and deliver a pacing pulse to the lead connector for delivery to the ventricular basal electrode to electrically stimulate the basal portion of the ventricle followed by a pacing pulse delivered by the lead connector to the ventricular apical electrode to electrically stimulate the apical portion of the ventricle during a cardiac cycle. The initial basal stimulation of the ventricles before applying the apical stimulation achieves a narrowing of the heart to get an efficient closure of the mitral and tricuspid valves. The valve closure is consequently triggered before the applied apical stimulation propagates over the ventricle muscle to cause a contraction and ejection of blood therein. The pacing pulse sequence consequently reduces the risk of valvular regurgitation through this initial basal stimulation prior to delivery of the pacing pulse in connection with the heart apex.

Another aspect relates to a method of delivering cardiac therapy to a heart by generating a pacing pulse that is applied to a basal portion of a heart ventricle followed after a defined time interval of generation and delivery of a pacing pulse to the apical portion of the heart ventricle. This novel pacing-based cardiac therapy provides an activation sequence to cause a cardiac movement that mimics the natural cardiac motion during the systolic part of the cardiac cycle.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present embodiments generally relates to implantable medical devices and method of operating such implantable medical devices (IMDs). In more detail, the IMDs are designed for applying cardiac therapy in terms of pacing pulses to the heart to achieve a more biologically relevant cardiac contraction pattern as compared to the traditional apex-to-base contraction pattern achieved by the prior art IMDs. As a result of the improved cardiac contraction pattern traditional problems of heart failure patients, such as regurgitation, in particular mitral regurgitation, can be reduced or mitigated. Additionally advantageous effects achievable through the novel operation of the IMD include improved cardiac performance.

The ventricular blood pumping function has traditionally been divided into a number of phases: i) an isovolumic contraction phase to develop preejection tension, ii) ejection, iii) a postejection isovolumic phase, and then iv) rapid and v) slow periods for filling.

Recent studies have concluded that the contractile mechanism of the heart and in particular the ventricles of the heart involve a number of separate steps including narrowing, shortening, lengthening, widening and twisting. In more detail, an initial global counterclockwise twist and attendant narrowing or "cocking" is taking place in the isovolumic contraction phase before ejection. This narrowing is followed by continuing counterclockwise twisting of the cardiac apex and clockwise twisting of the base as the ventricle longitudinally shortens during the ejection phase. A vigorous apical untwisting in the opposite direction then takes place as the ventricle lengthens and slightly widens during the isovolumic phase when no blood enters or leaves the ventricles. The apical untwisting motion is associated with a rapid ventricular pressure decay and continues into the rapid filling interval, when suction occurs together with an intraventricular pressure gradient until finally a phase of relaxation is taking place during diastole, when heart widening continues by slower filling before the atrium contracts prior to the next heart beat (*Circulation* 2008, 118: 2571-2587).

Thus, the cardiac motion begins in the base to narrow and elongate the ventricle before longitudinal shortening develops. The initial cardiac motion at the base before ventricular shortening is believed to be an important feature to reduce the mitral/tricuspid annular dimension and prevent mitral/tricuspid insufficiency and regurgitation once the ventricles shorten and blood is pumped out of the ventricles. An initial basal cardiac motion is therefore important to reduce the risk of unintentional blood leakage back into the atriums, which is a common problem for heart failure patients.

The traditional approach of pacing strategy for IMDs has been to stimulate the apex of the heart to initiate a depolarization wave movement and contraction pattern from the apex towards the ventricle base. With such a pacing strategy, there is no initial basal movement prior ventricular shortening that promotes efficient leaflet closing. This means that even though a search for "optimal" pacing site as in US 2004/0106958 or well-coordinate CRT therapy as in *Circulation Cardiovascular Imaging* 2009, 2: 444-450 can reduce the regurgitation risk slightly, the prior art techniques are flawed by achieving a ventricular contraction pattern that does not match the naturally occurring contraction sequence of healthy hearts as disclosed in the foregoing.

Embodiments as disclosed herein achieves a biologically relevant ventricular contraction pattern by delivery of a sequence of coordinated pacing pulses starting at or near the ventricular base and then at or close to the apex of the heart and ventricles and optionally continuing with further subsequent pacing sites continuing up towards the base. As a consequence of this novel pulse sequence, an initial pacing in connection with the valve plane will trigger the narrowing that is so important to achieve effective mitral/tricuspid valve closure before the apical pacing will trigger the shortening of the ventricles during blood ejection. The previously applied basal pacing will improve the chances of tight valve closure once this ventricular shortening and ejection is triggered by the apical pacing.

Figure 1:
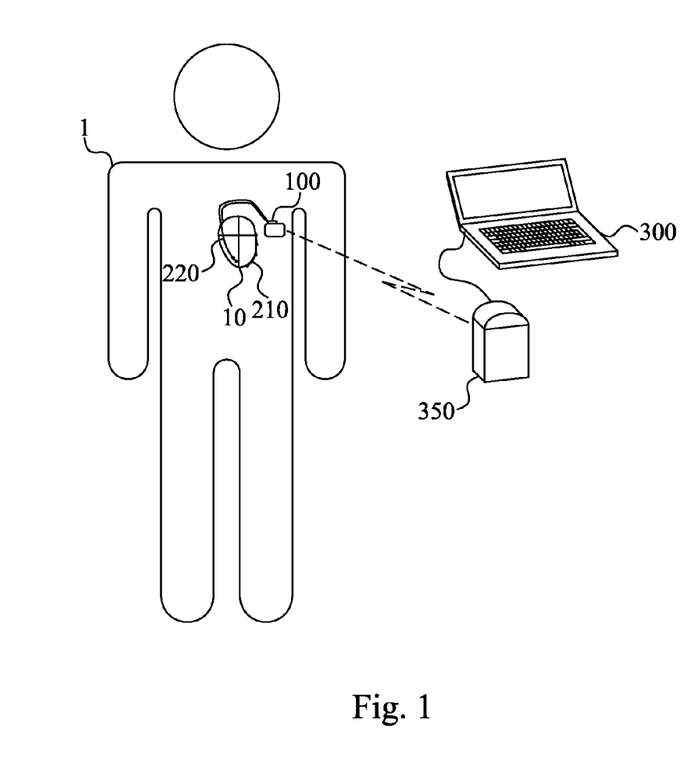
FIG. 1 is a schematic overview of a subject equipped with an implantable medical device according to an embodiment.

FIG. 1 is a schematic overview of a human patient 1 having an IMD 100. In the figure, the IMD 100 is illustrated as a device that monitors and/or provides therapy to the heart 10 of the patient 1, such as a pacemaker, cardiac defibrillator or cardioverter capable of delivering stimulating cardiac pacing therapy. The IMD 100 is, in operation, connected to one or more, two in the figure, cardiac leads 210, 220 inserted into or provided in connection with one or more heart chambers, preferably the left ventricle and/or right ventricle of the heart 10.

The figure also illustrates an external programmer or clinician's workstation 300 that can communicate with the IMD 100, optionally through a communication unit 350 that operates similar to a base station on behalf of the programmer 300. As is well known in the art, such a programmer 300 can be employed for transmitting IMD programming commands, causing a reprogramming of different operation parameters and modes of the IMD 100. Furthermore, the IMD 100 can upload diagnostic data descriptive of different medical parameters or device operation parameters collected by the IMD 100 to the programmer 300.

Figure 2:
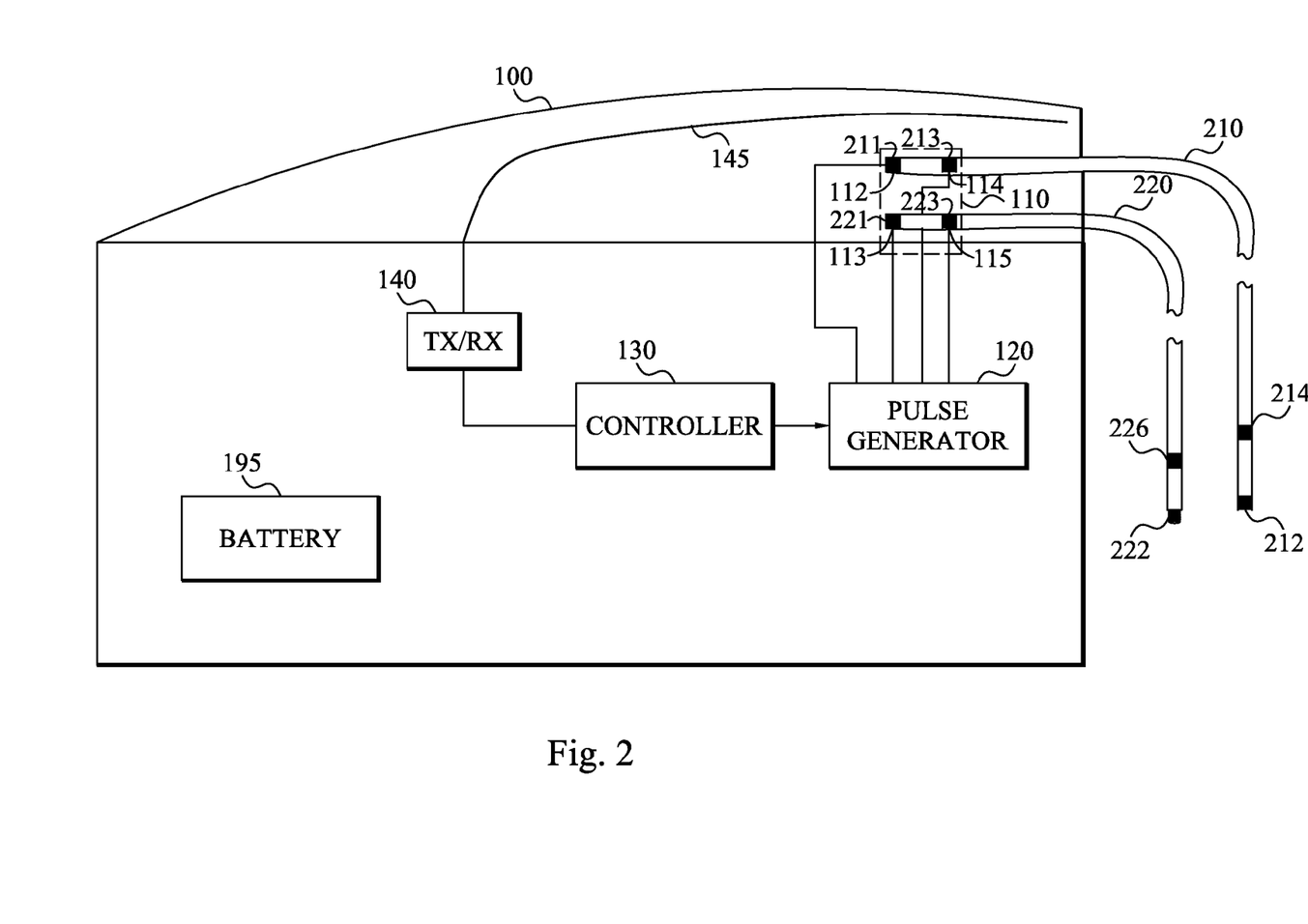
FIG. 2 is block diagram of an embodiment of an implantable medical device.

FIG. 2 is a schematic block diagram of an embodiment of an implantable medical device 100 capable of delivering cardiac therapy to a heart of a subject, in particular a mammalian subject and preferably a human patient.

The IMD 100 comprises a lead input or connector 110 configured to be, during operation in the subject body, electrically connectable to at least one cardiac lead 210, 220. The lead connector 110 consequently comprises terminals 112-115 that are electrically connected to matching electrode terminals 211, 213, 221, 223 of the cardiac lead 210, 220 when the cardiac lead 210, 220 is introduced in the lead connector 110. The at least one cardiac lead 210 comprises a ventricular basal electrode 214 designed to be implanted in connection with the left or right ventricle base when the cardiac lead 210 is inserted in the coronary sinus (or left ventricle) or the right ventricle of heart. A first electrode terminal 213 of the lead 210 is electrically connected to ventricular basal electrode 214 by a conductor running along the cardiac lead 210. The cardiac lead 210, 220 additionally comprises a ventricular apical electrode 212, 222 that is electrically connected to a second electrode terminal 211, 221 through another conductor running in the interior of the cardiac lead 210, 220. As the name indicates, the ventricular apical electrode 212, 222 will be placed in connection with the apex of the ventricle when the cardiac lead 210, 220 is implanted in the heart. In a typical embodiment, the ventricular apical electrode 212, 222 is a tip electrode 212, 222 present at the distal end of the cardiac lead 210, 220. The ventricular basal electrode 214 is then advantageously a ring electrode 214 provided at a distance from the distal end and towards the proximal end of the cardiac lead 210 that is connectable to the lead connector 110 of the IMD 100.

In the figure, the lead connector 110 is connectable to two cardiac leads 210, 220, such as a left ventricular lead 210 and a right ventricular lead 220. A left ventricular lead is typically implanted in the coronary sinus for safety reasons although implantation inside the left ventricle has been proposed in the art. In the following, "left ventricular lead" is used to describe a cardiac lead designed to deliver pacing pulses to the left ventricle regardless of its particular implantation site, e.g. inside the left ventricle or in the coronary sinus. The IMD 100 may alternatively be connected to a single cardiac lead, such as a left ventricular lead or a right ventricular lead, which is further described herein. In addition, the one or two (or indeed more) ventricular leads may be complemented with at least one atrial lead, such as a right atrial lead and/or a left atrial lead.

The IMD 100 comprises a pulse generator 120 connected to the lead connector 110. The pulse generator 120 is configured to generate pacing pulses that are applied to the heart through the at least one cardiac lead 210, 220.

A controller 130 is implemented in the IMD 100 for controlling the operation of the pulse generator 120. The controller 130 is configured to control the pulse generator 120 to deliver a pacing pulse sequence. This pacing pulse sequence comprises first a ventricular basal pulse followed by a ventricular apical pulse. The controller 130 therefore controls the pulse generator 120 to deliver a pacing pulse to a first terminal 114 that in turn is electrically connected to the ventricular basal electrode 214 followed by a pacing pulse to a second terminal 112, 113 that is electrically connected to the ventricular apical electrode 212, 222 of the cardiac lead 210, 220 during a cardiac cycle. The control of the pulse generator 120 conducted by the controller 130 will consequently lead to an initial electrical stimulation of the basal portion of the ventricle through the pulse delivered by the ventricular basal electrode 214 followed by electrical stimulation of the apical portion of the ventricle through the pulse delivered by the ventricular apical electrode 212, 222. The basal and apical pacing pulses are additionally delivered to the heart during the same cardiac cycle to trigger a biologically relevant contraction pattern of the ventricles with the initial narrowing in connection with the basal ventricular portion and then the shortening-triggering apical stimulation that causes the ventricles to eject the blood therein.

The IMD 100 also comprises a receiver 140 connected to an antenna 145, preferably a radio frequency (RF) antenna, and arranged for receiving data transmitted by the communication unit and the programmer to the IMD 100. The received data can include programming commands that cause a reprogramming of settings and/or operation parameters of the IMD 100. In a particular embodiment, these programming commands can affect the controller 130 in terms of coordinating the generation and delivery of the basal pacing pulse and the apical pacing pulse, which is described further herein.

Correspondingly, the IMD 100 also comprises a transmitter 140 connected to an antenna 145 and arranged for wirelessly transmit data to the communication unit and the programmer. The receiver and transmitter 140 can be respective dedicated receiver and transmitter or represent the receiving branch and the transmitting branch of a combined transmitting and receiving unit or transceiver 140. The IMD 100 can include one or more dedicated receiver antennas connected to the receiver 140 and one or more dedicated transmitter antennas connected to the transmitter 140. However, in most practical implementations one and the same antenna or antenna arrangement 145 is connected to both the receiver and transmitter or to the common transceiver 140.

A battery 195 is illustrated in the figure. The battery 195 provides operating power to all the circuits and units of the IMD 100. Batteries 195 for usage in IMDs 100 are well known in the art and are therefore not described in more detail herein.

FIG. 2 merely illustrates the units of an IMD 100 that are directly involved in embodiments as disclosed herein. It is therefore anticipated that the IMD 100 comprises additional units that are not illustrated in the figure and that are not directly involved in the operation of the disclosed embodiments.

The units and circuits of the IMD 100 may be provided as hardware or a combination of hardware and software. Alternatively, units of the IMD 100 are implemented in software. In such a case, a computer program product implementing the IMD 100 or a part thereof comprises software or a computer program run on a general purpose or specially adapted computer, processor or microprocessor of the IMD 100. The software includes computer program code elements or software code portions illustrated in FIG. 2. The program may be stored in whole or part, on or in one or more suitable computer readable media or data storage means such as hard discs, magneto-optical memory, in RAM or volatile memory, in ROM or flash memory.

Figure 3:
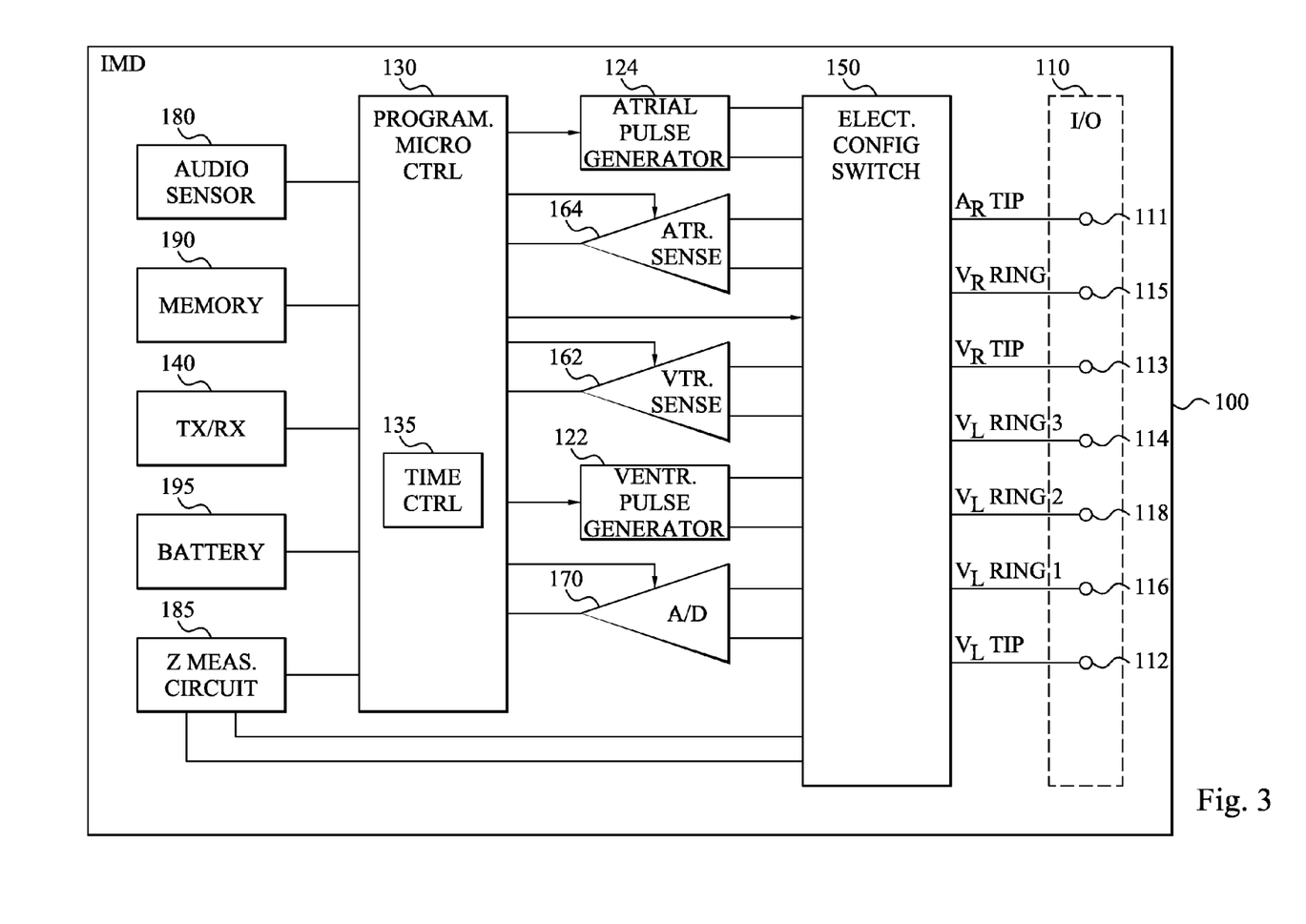
FIG. 3 is a block diagram of another embodiment of an implantable medical device.

FIG. 3 illustrates another embodiment of an IMD 100 suitable for delivering cardiac therapy to a heart of a subject. The figure is a simplified block diagram depicting various components of the IMD 100. While a particular multi-chamber device is shown in the figure, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination to provide an IMD capable of treating the appropriate ventricle(s) with pacing stimulation and optionally also cardioversion and/or defibrillation.

The IMD 100 comprises a housing, often denoted as can or case in the art. The housing can act as return electrode for unipolar leads, which is well known in the art. The IMD 100 also comprises the previously described lead connector 110 having, in this embodiment, a plurality of terminals 111-118.

For instance, in order to achieve right atrial sensing and pacing, the lead connector 110 comprises at least one terminal 111 designed to be connected to an atrial lead, such as a right atrial tip terminal 111 adapted for connection to an atrial tip electrode of the atrial lead. In order to achieve left chamber sensing and pacing, the connector lead comprises terminals 112, 114, 116, 118 connectable to a left ventricular lead. In the figure, the left ventricular lead is illustrated in the form of a multi-electrode lead and in particular a quadropolar lead. The lead consequently comprises a tip electrode that is electrically connectable to a left ventricular tip terminal 112 and three spatially separated ring electrodes, each of which is electrically connectable to a respective left ventricular ring electrode terminal 114, 116, 118 of the lead connector 110.

In order to support right chamber sensing and pacing, the connector lead 110 further comprises a right ventricular tip terminal 113 and a right ventricular ring terminal 115, which are adapted for connection to a right ventricular tip electrode and a right ventricular ring electrode of a right ventricular lead.

In alternative embodiments, the IMD 100 is, in operation, connected to a right ventricular lead or a left ventricular lead, which can be of traditional design, i.e. comprising a tip electrode and a single ring electrode. Alternatively, the right or left ventricular lead can be in the form of a multi-electrode lead, such as a quadropolar lead. Alternatively, the IMD 100 is connected to both a left ventricular lead and one or more right ventricular leads. Additionally, an atrial lead, typically a right atrial lead may be connected to the IMD 100 as illustrated in FIG. 3.

The IMD 100 also comprises a controller 130, preferably in the form of a programmable microcontroller 130 that controls the operation of the IMD 100. The controller 130 typically includes a microprocessor, or equivalent control circuitry, designed specifically for controlling the delivery of pacing therapy, and may further include RAM or ROM memory, logic and timing circuitry, state machine circuitry, and input/output (I/O) circuitry. Typically, the controller 130 is configured to process or monitor input signal as controlled by a program code stored in a designated memory block. The type of controller 130 is not critical to the described implementations. In clear contrast, any suitable controller may be used that carries out the functions described herein. The use of microprocessor-based control circuits for performing timing and data analysis functions are well known in the art.

The IMD 100 as illustrated in FIG. 3 comprises an atrial pulse generator 124 and a ventricular pulse generator 122 that generate pacing pulses for delivery by the atrial lead and the left/right ventricular lead through an electrode configuration switch 150.

It is understood that in order to provide stimulation therapy in different heart chambers, the atrial and ventricular pulse generators 122, 124 may include dedicated, independent pulse generators, multiplexed pulse generators, or shared pulse generators (as has been illustrated in FIG. 2). The pulse generators 122, 124 are controlled by the controller 130 via appropriate control signals, respectively, to trigger or inhibit the stimulation pulses.

The controller 130 further includes timing control circuitry 135 to control the timing of the stimulation pulses, such as pacing rate, atrio-ventricular (AV) delay, atrial interconduction (AA) delay, or ventricular interconduction (W) delay, etc. as well as to keep track of the timing of refractory periods, blanking intervals, noise detection windows, evoked response windows, alert intervals, marker channel timing, etc., which is well known in the art. In a particular embodiment the timing control circuitry 135 is employed by the IMD 100 for determining suitable time intervals between the initial basal stimulation and the following apical stimulation during the same cardiac cycle.

An electronic configuration switch 150 preferably includes a plurality of switches for connecting the desired electrodes to the appropriate I/O circuits, thereby providing complete electrode programmability. Accordingly, the electronic configuration switch 150, in response to a control signal from the controller 130, determines the polarity of the stimulation pulses (e.g., unipolar, bipolar, combipolar, etc.) by selectively closing the appropriate combination of switches (not shown) as is known in the art.

Atrial sensing circuits 164 and ventricular sensing circuits 162 may also be selectively coupled to the right atrial lead and the left/right ventricular lead through the switch 150 for detecting the presence of cardiac activity in the heart chambers. Accordingly, the atrial and ventricular sensing circuits 162, 164 may include dedicated sense amplifiers, multiplexed amplifiers, or shared amplifiers. The switch 150 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 162, 164 preferably employs one or more low power, precision amplifiers with programmable gain and/or automatic gain control, band-pass filtering, and a threshold detection circuit, as known in the art, to selectively sense the cardiac signal of interest.

The outputs of the atrial and ventricular sensing circuits 162, 164 are connected to the controller 130, which, in turn, is able to trigger or inhibit the atrial and ventricular pulse generators 122, 124, respectively, in a demand fashion in response to the absence or presence of cardiac activity in the appropriate chambers of the heart.

Furthermore, the controller 130 is also capable of analyzing information output from the sensing circuits 162, 164 and/or a data acquisition system 170 to determine or detect whether and to what degree tissue capture has occurred and to program a pulse, or pulse sequence, in response to such determinations. The sensing circuits 162, 164, in turn, receive control signals over signal lines from the controller 130 for purposes of controlling the gain, threshold, polarization charge removal circuitry, and the timing of any blocking circuitry coupled to the inputs of the sensing circuits 162, 164 as is known in the art.

Cardiac signals are also applied to inputs of an analog-to-digital (A/D) data acquisition system 170. The data acquisition system 170 is configured to acquire intracardiac electrogram signals, convert the raw analog data into a digital signal, and store the digital signals for later processing and/or telemetric transmission to the programmer. The data acquisition system 170 is coupled to the atrial lead, the left ventricular lead and/or the right ventricular lead through the switch 150 to sample cardiac signals across any pair of desired electrodes.

The controller 130 is further coupled to a memory 190 by a suitable data/address bus, wherein the programmable operating parameters used by the controller 130 are stored and modified, as required, in order to customize the operation of the IMD 100 to suit the needs of a particular patient. Such operating parameters define, for example, pacing pulse amplitude, pulse duration, electrode polarity, rate, sensitivity, automatic features, and time interval between pacing pulse of an applied pacing pulse sequence.

Advantageously, the operating parameters of the IMD 100 may be non-invasively programmed into the memory 190 through a transceiver 140 in communication via a communication link with the previously described communication unit of the programmer. The controller 130 activates the transceiver 140 with a control signal.

The IMD 100 additionally includes a battery 195 that provides operating power to all of the circuits shown in FIG. 3.

The biologically relevant pacing therapy of the IMD by an initial ventricular basal stimulation before delivering pacing pulse to the apex of the ventricles will now be described in more detail to FIGS. 4A to 11B illustrating different implementation embodiments with different lead and electrode configurations that can be used for the IMD.

Figure 4A:
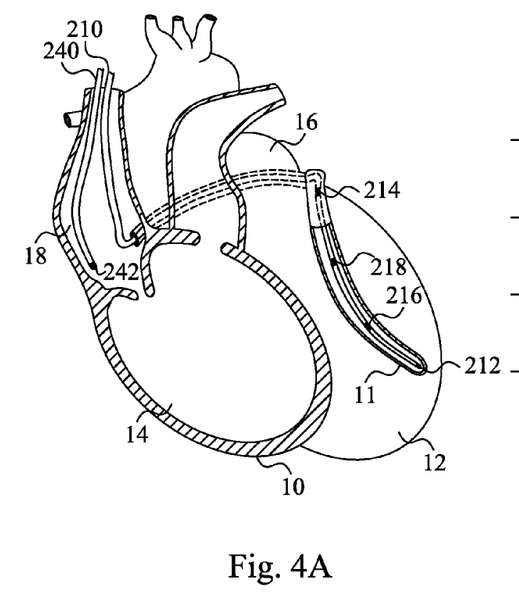
FIG. 4A illustrates a cardiac lead connectable to an implantable medical device according to an embodiment.

FIG. 4A illustrates a human heart 10 with a left ventricular lead 210 of quadropolar type implanted in the coronary sinus 11 in connection with the left ventricle 12. The quadropolar lead 210 comprises a tip electrode 212 at its distal end and three ring electrodes 214, 216, 218 arranged at different positions on the lead 210. One of these ring electrodes 214, preferably the most proximal one, is provided in connection with the basal portion of the ventricle 12 when the lead 210 is correctly implanted in the coronary sinus 11. The two other ring electrodes 216, 218 are then provided on the lead 210 between the tip electrode 212 and the basally positioned ring electrode 214.

With this type of ventricular lead the controller of the IMD is configured to control the pulse generator and the switch to deliver a pacing pulse to the terminal of the lead connector electrically connected to the ventricular basal electrode 214 of the lead 210, followed by a pacing pulse to the terminal electrically connected to the ventricular apical electrode 212 and then to the terminals electrically connected to a respective middle ring electrode 216, 218 first to the most distal ring electrode 216 and then the most proximal of the two ring electrodes 218.

Figure 4B:
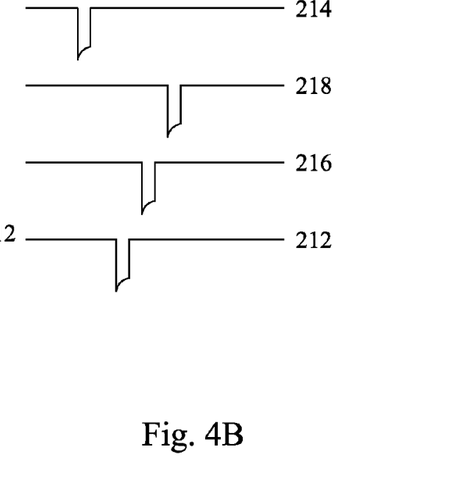
FIG. 4B illustrates a sequence of stimulating pacing pulses applied to the heart using the cardiac lead illustrated in FIG. 4A.

FIG. 4B illustrates the resulting pacing pulse sequence from this embodiment of operation by the controller. Thus, the first pacing pulse of the ventricular pacing pulse sequence is applied to the basal portion of the ventricle 12 by the most proximal ring electrode 214. The second pacing pulse is applied to the apical portion of the ventricle 12 by the distal tip electrode 212. Thereafter the third pacing pulse is applied by the most distal ring electrode 216 followed by the fourth pacing pulse that is delivered by the middle ring electrode 218. As is seen from FIG. 4B, the applied electrical stimulation starts at the basal portion and then jumps to the apical portion of the ventricle 12 to continue upwards towards the basal portion. This sequence of pacing pulses correctly mimics the biological movement of the heart during contraction with the initial basal narrowing prior the shortening of the ventricles 12, 14 to eject the blood out from the ventricles 12, 14.

It is anticipated by the present invention that even though the cardiac lead 210 comprises four electrodes 212, 214, 216, 218 in this embodiment not all of them needs to be used when delivering a pacing pulse sequence. For instance, the pacing pulse(s) applied to one or both of the two most distal ring electrodes 216, 218 can be skipped. In such a case, the pulse sequence starts with the basal pacing pulse followed by the apical pacing pulse and optionally one of the pacing pulse applied to the middle portion of the ventricle 12.

Generally, by applying the stimulation pulse to the apex portion of the ventricle 12, the resulting depolarization wave will travel from the stimulation site towards the basal portion of the ventricles 12, 14. It may therefore be enough to only have the initial basal ventricular stimulation followed by the apical ventricular stimulation to get an effective depolarization wave propagation and contraction of the ventricle muscle. However, in some patients the depolarization wave will not propagate correctly over the ventricles 12, 14, for instance due to a prior ischemic damage to part of the cardiac muscle. For these patients it can therefore be advantageous to deliver pacing pulses to one or both the ring electrodes 216, 218 provided in the middle portion of the ventricle 12 to get the desired apical-to-base depolarization propagation after the initial basal stimulation.

FIG. 4A additionally illustrates that the IMD can be connectable to an atrial lead 240, here represented by a right atrial lead 240 having at least one electrode 242. The atrial lead 240 can be used for atrial sensing and pacing as is well known in the art in additional to the novel operation of the IMD in relation to ventricular pacing. In another embodiment, the atrial lead 240 is not necessary implanted in the right atrium 18 of the heart 10 but can instead be provided in the left atrium 16. Also a combination of right and left atrial leads 240 is possible.

Figure 5A:
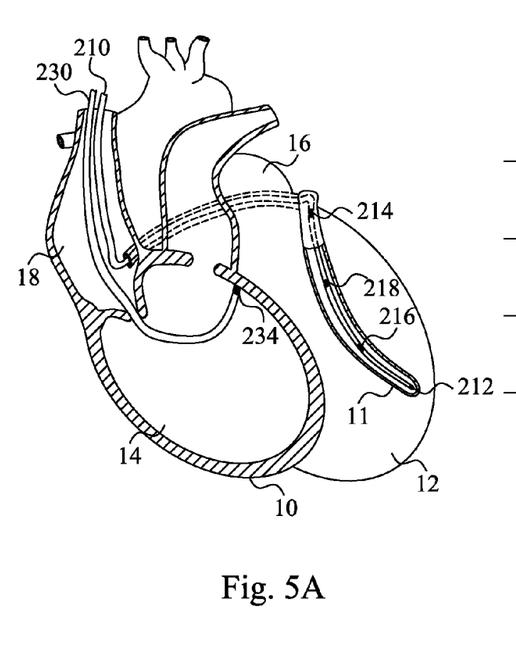
FIG. 5A illustrates a set of cardiac leads connectable to an implantable medical device according to an embodiment.

FIG. 5A illustrates the quadropolar left ventricular lead 210 of FIG. 5A complemented with a right ventricular lead 230 implanted in the right ventricle 14 of the heart 10. In this particular embodiment, the right ventricular lead 230 is implemented to have an electrode 234, such as its tip electrode 234, anchored close the basal portion of the right ventricle 14. For instance, the right ventricular lead 230 can be anchored in and attached to the upper part of the septum separating the two ventricles 12, 14.

Figure 5B:
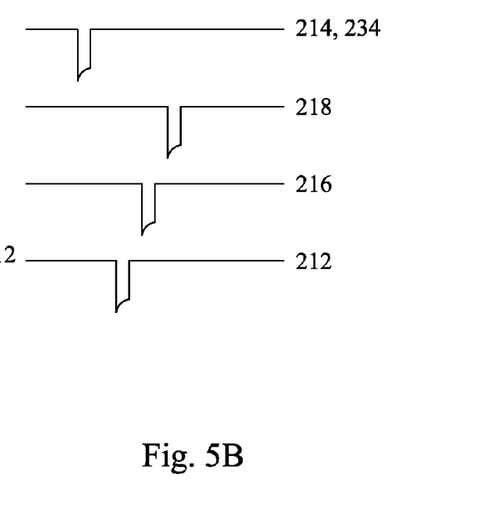
FIG. 5B illustrates a sequence of stimulating pacing pulses applied to the heart using the cardiac lead set illustrated in FIG. 5A.

The controller of the IMD is in this embodiment configured to control the pulse generator and the switch to first deliver a pacing pulse to the terminal of the lead connector that is electrically connected through the left ventricular lead 210 to the ring electrode 214 positioned in connection with the basal portion of the left ventricle 12 and a pacing pulse to the terminal that is electrically connected through the right ventricular lead 230 to its tip electrode 234. In a preferred embodiment, the pacing pulses are applied substantially simultaneously to the two electrode terminals to get a coordinated and preferably synchronized stimulation of the basal portions of the left and right ventricles 12, 14, which is schematically illustrated in FIG. 5B. The controller also controls the pulse generator and the switch to continue by generating and delivering a pacing pulse to the tip electrode 212 of the left ventricular lead 210 to electrically stimulate the apex of the heart followed by optional pacing pulses that are delivered to the middle portion of the ventricles 12, 14 by the ring electrodes 216, 218 in an apex-to-base sequence as illustrated in FIG. 5B.

Figures 6A, 6B:
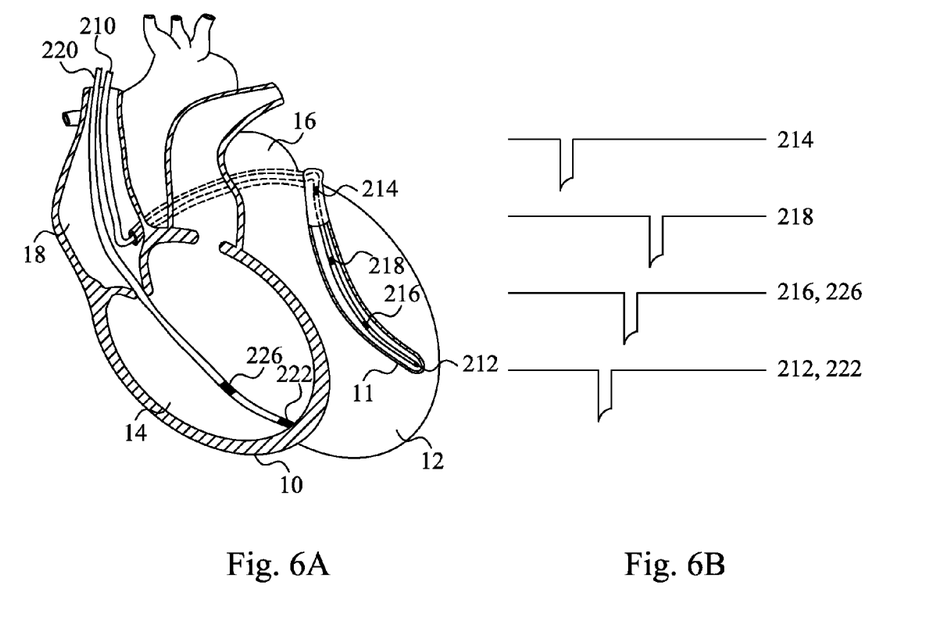
FIG. 6A illustrates a set of cardiac leads connectable to an implantable medical device according to another embodiment.
FIG. 6B illustrates a sequence of stimulating pacing pulses applied to the heart using the cardiac lead set illustrated in FIG. 6A.

FIG. 6A illustrates a further embodiment with a right ventricular lead 220 having a tip electrode 222 anchored in the right ventricle 14 in connection with the heart apex. The right ventricular lead 220 may optionally also comprise at least one ring electrode 226 more proximally placed on the lead 220 as compared to the tip electrode 222.

During operation the controller of IMD controls the pulse generator and switch to first generate and deliver a pacing pulse to the basal portion of the left ventricle through the ring electrode 214. A respective pacing pulse is then generated and coordinated for preferably synchronized delivery to the tip electrodes 212, 222 of the two lead 210, 220 to electrically stimulate the apices of the ventricles 12, 14 before the pacing pulse sequence optionally continues with the most distal ring electrode 216 and the middle ring electrode 218 of the left ventricular lead 210, see FIG. 6B. If the right ventricular lead 220 comprises at least one ring electrode 226, a pacing pulse can be delivered thereto to stimulate the middle portion of the right ventricle 14. The pacing pulse delivery to the ring electrode 226 is preferably synchronized with delivery of a pacing pulse to one of the ring electrodes 216 of the left ventricular lead 210 to get a synchronized stimulation of the middle portions of the two ventricles 12, 14 after the apices have been stimulated.

Figures 7A, 7B:
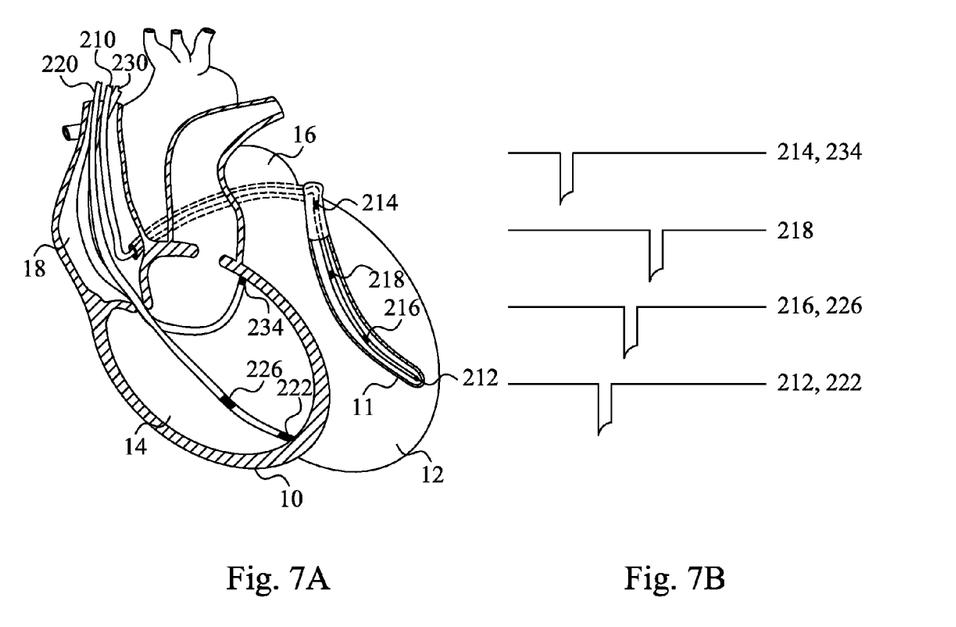
FIG. 7A illustrates a set of cardiac leads connectable to an implantable medical device according to a further embodiment.
FIG. 7B illustrates a sequence of stimulating pacing pulses applied to the heart using the cardiac lead set illustrated in FIG. 7A.

FIG. 7A is an embodiment basically illustrating a combination of the lead configuration of FIGS. 5A and 6A. Thus, in this case a first right ventricular lead 230 is implanted in the right ventricle 14 to have an electrode 234 positioned close the basal portion of the right ventricle 12. A second right ventricular lead 220 comprises an electrode 222 for achieving stimulation of the right ventricular apex and optionally at least one further electrode 226 for stimulation at a middle portion of the right ventricle 14.

With the lead configuration of FIG. 7A, the controller is preferably configured to control the pulse generator and the switch to first deliver and apply respective pacing pulses to the basal portions of the ventricles 12, 14 followed by the apical portions of the ventricles 12, 14 and optionally the middle portions. The resulting pacing pulse sequence is illustrated in FIG. 7B. In an embodiment, the pacing pulses to the ring electrode 214 and the tip electrode 234 are synchronized, as are the pacing pulses to the tip electrodes 212, 214 and the ring electrodes 216, 226 if these two latter a used.

In FIGS. 4A, 5A, 6A and 7A a quadropolar left ventricular lead has been used either alone or complemented with one or two right ventricular leads. In alternative embodiments, a quadropolar right ventricular lead can instead be used either alone or complemented with a left ventricular lead. It is also possible to use both a quadropolar left ventricular lead and a quadropolar right ventricular lead. Furthermore, the multi-electrode lead does not necessarily have to be a quadropolar lead but can have any multiple number of electrodes, such as three, four, five, six, seven, eight, nine, ten or even more. Any of the embodiments illustrated in FIGS. 5A, 6A and 7A may also be complemented with one or more atrial leads as illustrated in FIG. 4A.

Figure 8A:
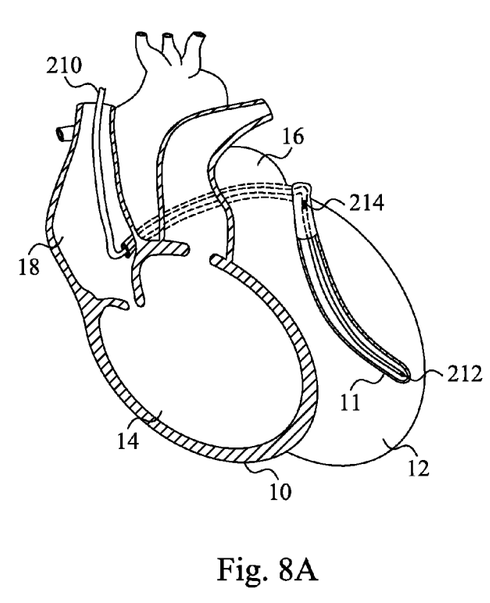
FIG. 8A illustrates a cardiac lead connectable to an implantable medical device according to another embodiment.
Figure 8B:
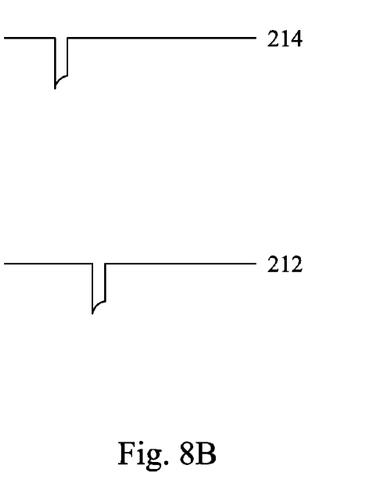
FIG. 8B illustrates a sequence of stimulating pacing pulses applied to the heart using the cardiac lead illustrated in FIG. 8A.

The novel pacing pulse sequence of the IMD must not necessarily be delivered by means of a multi-electrode lead. FIG. 8A illustrates a left ventricular lead 210 having a basal electrode 214 and an apical electrode 212. In this embodiment as illustrated in FIG. 8B, the controller controls the pulse generator and the switch to generate and deliver a pacing pulse to the basal electrode 214 followed after a time interval by a pacing pulse to the apical portion 212.

Figure 9A:
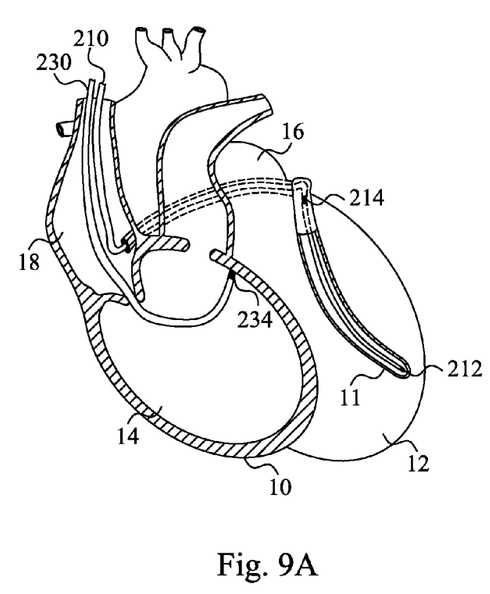
FIG. 9A illustrates a set of cardiac leads connectable to an implantable medical device according to yet another embodiment.
Figure 9B:
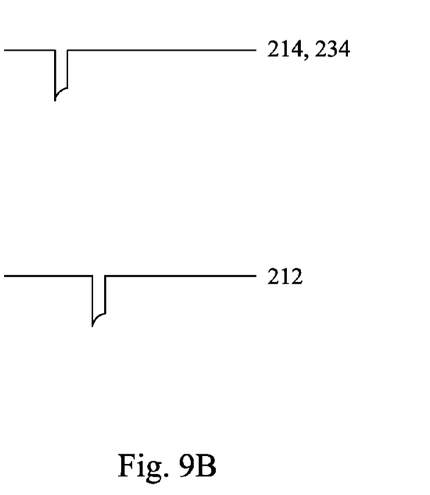
FIG. 9B illustrates a sequence of stimulating pacing pulses applied to the heart using the cardiac lead set illustrated in FIG. 9A.

FIG. 9A illustrates a lead configuration with the left ventricular lead 210 of FIG. 8A complemented by a right ventricular lead 230 having a basal electrode 234 as discussed above in connection with FIG. 5A. In this case, the pacing pulse sequence is preferably generated by the pulse generator and controlled by the controller to get a coordinated delivery of a respective pacing pulse to the basal electrodes 214, 234 followed by delivery of a pacing pulse to the apex of the left ventricle 12 by the apical electrode 212, which is schematically illustrated in FIG. 9B.

Figure 10A:
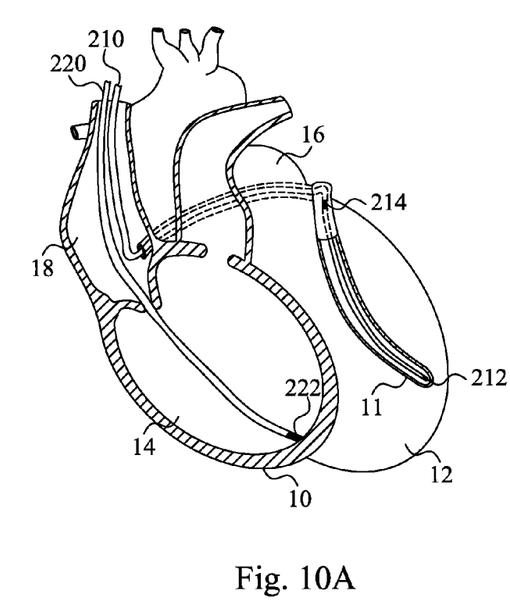
FIG. 10A illustrates a set of cardiac leads connectable to an implantable medical device according to an additional embodiment.
Figure 10B:
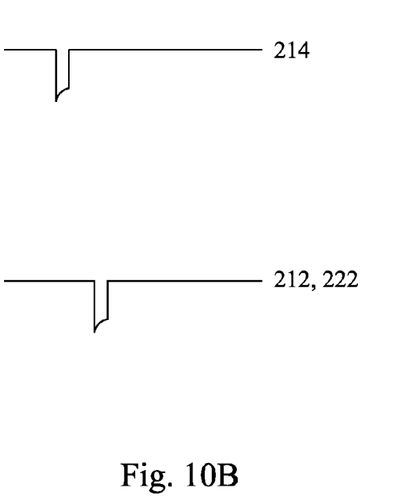
FIG. 10B illustrates a sequence of stimulating pacing pulses applied to the heart using the cardiac lead set illustrated in FIG. 10A.

In FIG. 10A, the right ventricular lead 220 is now implanted to have an electrode 222 anchored in connection with the apex of the right ventricle 14 instead of in connection with the basal portion. FIG. 10B illustrates a preferred pacing pulse sequence with the initial stimulation of the basal portion of the ventricles 12, 14 through the basal electrode 214 followed by the coordinated stimulation of the apical portions by the apical electrodes 212, 222.

Figure 11A:
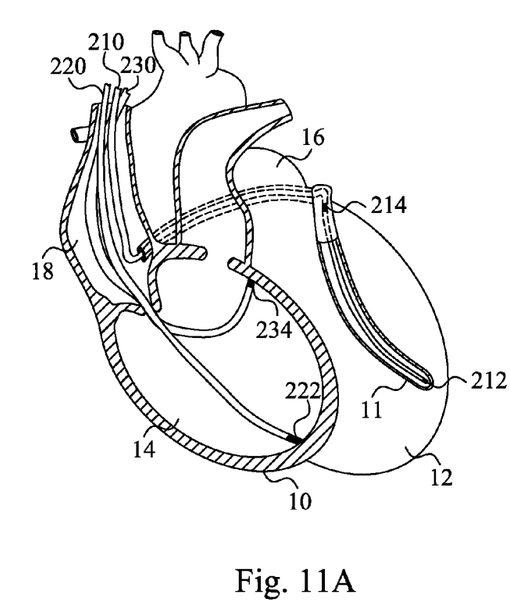
FIG. 11A illustrates a set of cardiac leads connectable to an implantable medical device according to yet a further embodiment.
Figure 11B:
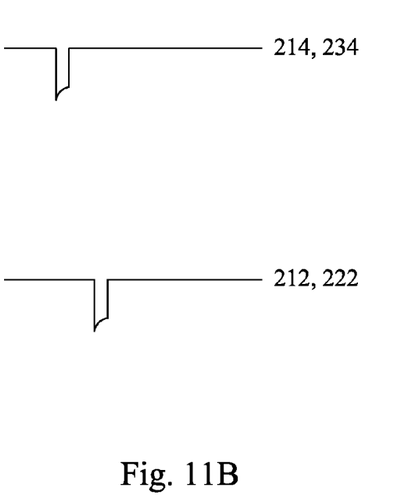
FIG. 11B illustrates a sequence of stimulating pacing pulses applied to the heart using the cardiac lead set illustrated in FIG. 11A.

FIG. 11A is basically a combination of the lead configurations of FIGS. 9A and 10A. Thus, the left ventricular lead 210 is complemented with two right ventricular leads 220, 230 one having a basal electrode 234 and one having an apical electrode 222. The pacing pulse sequence according to a preferred embodiment is illustrated in FIG. 11B for this lead configuration. Thus, respective pacing pulses are delivered and coordinated by the IMD for delivery to the basal portions of the ventricles 12, 14 followed by atrial stimulation at the ventricle apices.

The right ventricular lead 220 having an apical electrode 222 in FIGS. 10A and 11A can also be complemented with at least one ring electrode as illustrated in FIGS. 6A and 7A to also stimulate the middle portion of the right ventricle 14.

Additionally, one or more atrial leads can also be used in connection with any of the lead configurations of FIGS. 8A, 9A, 10A and 11A.

Figure 13:
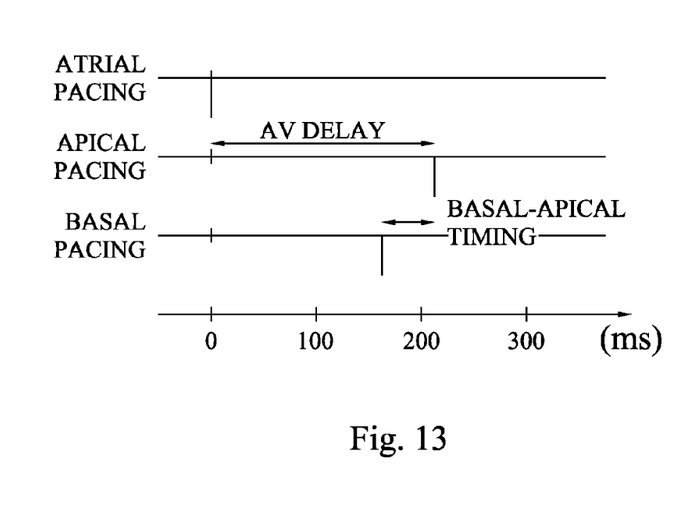
FIG. 13 is a diagram schematically illustrating timing between delivery of atrial, ventricular basal and apical pulses.

FIG. 13 is a timing diagram illustrating a case with both atrial and ventricular pacing. In the diagram an atrial pacing pulse is first delivered at which time an atrio-ventricular (AV) interval is started. If atrial sensing instead indicated a spontaneous electric event in the atrium the atrial pacing is blocked. In the art, once the AV interval has elapsed and no electric event is sensed in the ventricles, a pacing pulse is delivered to the ventricle, typically at the apical portion. However, according to the present invention a pacing pulse is first applied to the basal portion of the ventricle before the apical pacing of the ventricle.

In an embodiment, the basal stimulation is performed prior expiry of the traditional AV interval so that the basal portion of the ventricles is stimulated before a pacing pulse is applied to the apical portion. Generally, the time interval between the initial basal stimulation and the apical stimulation can be from about 10 ms to about 100 ms, such as about 50 to 100 ms. The reason why the traditional AV delay can be used in connection with the embodiments is that the initial basal stimulation is not intended to cause the stimulation-triggered contraction and ejection but is instead mainly intended to trigger a narrowing in connection with the basal ventricular portions to form an efficient closure of the mitral and tricuspid valves before the apical stimulation causes the propagation of a depolarization wave over the ventricles that leads to contraction and shortening of the ventricles and ejection of the blood therein. In a preferred embodiment, the basal stimulation therefore occurs prior to expiry of the traditional AV interval.

The time interval from basal stimulation to apical stimulation, denoted basal-apical timing in the figure, can be a predefined parameter that is programmed into the IMD. In an alternative approach, the time interval can be adjusted to be suited and adapted to the particular patient.

For instance, during patient follow-ups or other times when the IMD patient visits a clinic an optimal basal-apical timing can be determined. The timing for patients suffering from mitral and/or tricuspid valve regurgitation can be determined with the objective of minimizing the severity of regurgitation. In the following different techniques for conducting such optimization are briefly described.

For instance, an echocardiogram or cardiac ultrasound can be recorded to get a two dimensional (2D) trans-thoracic echocardiogram (TTE), a multi-plane trans-esophageal echocardiogram (TEE) or a three-dimensional (3D) echocardiogram of the heart. This allows assessment of cardiac valve areas and function and any leaking of blood through the valves.

Alternatively regurgitant flow can be followed by eyeballing, for example, 2D TTE with color flow Doppler. Regurgitant flow can be quantified by different measurable parameters such as vena cava contracta width, regurgitant volume, regurgitant fraction, effective regurgitant orifice area, see *European Journal of Echocardiography* 2003, 4: 237-261.

Also magnetic resonance imaging (MRI) can be used to quantify regurgitant volumes as disclosed in *European Journal of Cardiothoracic Surgery* 2005, 27: 462-467.

A further example is measuring heart sound to detect a leaking blood flow through the mitral and/or tricuspid valve. Heart sound measurements can be performed with esophageus microphones or transthoracic auscultation.

In an optimization procedure the following process step can be performed. A fixed AV interval is determined for the procedure. Different programmable basal-apical timing intervals are tested to find the optimal one in terms of minimizing regurgitation. For each such programmable timing interval, first only apical pacing is applied to the ventricle according to the prior art in order to get a baseline measure of the regurgitation parameter. Thereafter the same measurements are conducted but with the current programmable basal-apical timing interval to be tested to get a test measure. The change from the baseline measure is derived. The basal-apical timing interval resulted in the best or optimal change from the baseline in terms of minimizing regurgitation is then selected and used as optimal basal-apical timing interval.

The physician then uses the programmer to send a parameter reprogram command through the communication unit to the receiver 140 of the IMD 100 as illustrated in FIGS. 2 and 3. The controller 130 uses this received reprogram command to set the optimal interval between basal stimulation and the end of the AV delay and the apical stimulation. The time controller 135 of the IMD 100 uses the reprogrammed time parameter for determining when activation control signals are to be sent to the ventricular pulse generator 122.

In another embodiment, the IMD 100 itself can determine optimal basal-apical timing parameter through a closed loop optimization. The IMD 100 therefore optionally comprises a physiological sensor 180 capable of recording a parameter indicative of regurgitation. In an illustrative example this physiological sensor 180 is in the form of a microphone or audio or acoustic sensor capable of recording heart sounds. The audio sensor 180 may in particular record the sound of valve closure, any leaking blood flow through the mitral and/or tricuspid valves and the blood flow through the aortic and/or pulmonary valves.

The controller 130 is then configured to determine a suitable time interval between delivery of basal pacing and apical pacing based on the recorded audio signal, such as an audio signal representing leaking blood flow from the ventricles to the atria.

Instead of or as a complement to heart sound based sensing, the IMD 100 comprises an impedance measuring circuit 185 configured to determine an impedance parameter representative of the blood volume in an atrium, such as the right atrium, through an intracardiac or intrathoracic impedance signal.

For instance, the atrial pulse generator 124 can be configured to generate a current pulse that is applied to at least a portion of the atrium, such as between a tip and ring electrode of the atrial lead or between the tip electrode of the atrial lead and the case electrode. The impedance measuring circuit 185 is then configured to determine a voltage signal resulting from the applied current pulse. In this case bipolar, tripolar or quadropolar impedance measurements can be performed. The impedance measuring circuit 185 further determines atrial impedance based on the current pulse and the voltage signal. The determined atrial impedance is preferable representative of the blood volume present inside the atrium. The atrial impedance during the systolic part of the heart cycle is particularly suitable for detecting any leakage of blood from the ventricle into the atrium, resulting in a decrease in the atrial impedance amplitude. In such a case, a reference atrial impedance signal has preferably previously been recorded at a time point when no regurgitation occurred. Valve insufficiency can then be determined based on a comparison between the determined atrial impedance and the reference atrial impedance.

The time controller 135 determines an optimal basal apical timing based on the determined atrial impedance.

Also intracardiac impedance reflecting the volume of the right or left ventricles can be used. For instance, right ventricular bipolar, right ventricular unipolar, right ventricular-left ventricular quadropolar and left ventricular bipolar impedance vectors can be used to measure the systolic slope of the cardiogenic impedance signal. This slope represents the rate of change of the ventricular volume, $$\frac{dV}{dt},$$

and will increase with increased valvular regurgitation.

A further well established parameter within the field of cardiac rhythm therapy is $$\left(\frac{dp}{dt}\right)_{max}.$$

When blood is leaking back into the atrium at regurgitation, $$\left(\frac{dp}{dt}\right)_{max}$$

is reduced. This means $$\left(\frac{dp}{dt}\right)_{max}$$

can be a parameter that is monitored in order to determine optimal basal-apical timing. Determination of $$\left(\frac{dp}{dt}\right)_{max}$$

by an implantable medical device is well known in the art, using for instance piezoelectric-based and other pressure sensors, and is not further described herein.

Additionally, a combination of $$\frac{dV}{dt} \text{ and } \left(\frac{dp}{dt}\right)_{max}$$

can also be used.

$$\frac{dV}{dt}$$

will increase while $$\left(\frac{dp}{dt}\right)_{max}$$

decreases at atrioventricular valve regurgitation. A combination of these two parameters will increase the specificity and the sensitivity to changed basal-apical timings.

In similarity to the previously described clinically based optimization procedure, the IMD 100 can be configured to test different reprogrammable basal-apical timing values and determine the regurgitation representative parameter based on the audio signal, $$\left(\frac{dp}{dt}\right)_{max}$$

or atrial impedance for each of the timing values. The timing value minimizing regurgitation is then selected and used as basal-apical timing interval for the IMD 100.

The optimization procedure of the IMD 100 can be conducted periodically at scheduled test intervals. Alternatively, the optimization procedure can be started based on an optimization request received by the receiver 140 and originating from the programmer.

Instead of or as a complement to optimization of the basal-apical timing based on the objective of minimizing regurgitation, other optimization objectives can be used. For instance, maximization of cardiac performance in terms of maximizing cardiac output is such a preferred optimization criterion.

At a clinic, effective cardiac output and effective stroke volume can be monitored by measuring transthoracic impedance of the patient. Alternatively, blood flow measurements, for instance, representing aortic flow or carotid flow can be used as indication of cardiac output. The previously mentioned echocardiograph and MRI systems can also be used to assess cardiac output and detect changes in cardiac output when testing different basal-apical timing intervals for the purpose of identifying such a timing interval that maximizes cardiac output.

In similarity to the optimization of the basal-apical timing by the IMD for the purpose of minimizing valvular regurgitation, the IMD can also be designed for conducting a closed loop optimization with the objective of maximizing effective cardiac output. The previously mentioned audio sensor or impedance measuring circuit can be used to monitor parameters representative of cardiac output and cardiac performance, such as effective stroke volume by intracardiac impedance measurements. Another possibility is to have an accelerometer, such as endocardial accelerometer provided in the IMD or connected thereto to adjust the basal-apical timing in order to optimize the peak endocardial acceleration.

Figure 12:
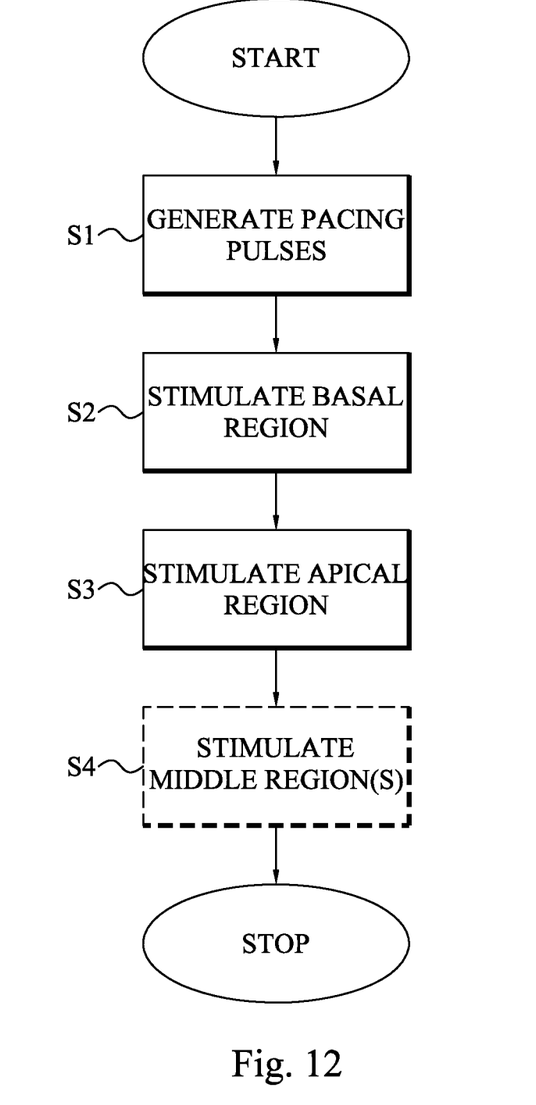
FIG. 12 is flow diagram illustrating a method of applying therapy to a heart of a subject.

FIG. 12 is a flow diagram illustrating a method of delivering cardiac therapy to a heart of a subject. The method starts in step S1, where a sequence of pacing pulses is generated. A next step S2 stimulates the basal portion of a ventricle or both ventricles of the heart by delivering a pacing pulse to this basal portion. After a defined basal-apical timing interval the apical portion of the ventricle or ventricles is stimulated by delivering a pacing pulse to the apical portion in step S3. In an optional embodiment, one or more middle regions of the ventricle or ventricles may then be stimulated with further pacing pulses during the cardiac cycle. In such a case, these optional pacing pulses are preferably delivered in an apex-to-base manner if multiple sites of the middle ventricular portion are stimulated. The method then ends or continues to a next cardiac cycle where a new pacing pulse sequence can be generated and delivered to the heart.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. An implantable medical device for delivering cardiac therapy to a heart of a subject comprising:
a lead connector having i) a first terminal electrically connectable to a first electrode terminal of a quadropolar ventricular lead, ii) a second terminal electrically connectable to a second electrode terminal of said quadropolar ventricular lead, iii) a third terminal electrically connectable to a first middle electrode terminal of said quadropolar ventricular lead, and iv) a fourth terminal electrically connectable to a second middle electrode terminal of said quadropolar ventricular lead, said quadropolar ventricular lead having a ventricular basal electrode electrically connected to said first electrode terminal and being adapted for implantation in connection with a basal portion of a ventricle of said heart, a ventricular apical electrode electrically connected to said second electrode terminal and being adapted for implantation in connection with an apical portion of said ventricle, a first ventricular middle electrode electrically connected to said first middle electrode terminal and a second ventricular middle electrode positioned on said quadropolar ventricular lead between said first ventricular middle electrode and said ventricular basal electrode and electrically connected to said second middle electrode terminal; and;
a pulse generator connected to said lead connector and configured to generate pacing pulses; and
a controller connected to said pulse generator and configured to control said pulse generator to deliver a pacing pulse to said first terminal followed by a pacing pulse to said second electrode terminal, followed by a pacing pulse to said third terminal and followed by a pacing pulse to said fourth terminal during a cardiac cycle.

2. The implantable medical device according to claim 1, wherein said controller is configured to control said pulse generator to deliver, during said cardiac cycle, said pacing pulse to said first terminal followed by said pacing pulse to said second terminal after a time period of from 10 ms to 100 ms from the delivery of said pacing pulse to said first terminal.

3. The implantable medical device according to claim 1, further comprising an audio sensor configured to record an audio signal associated with a backward flow of blood out from said ventricle, wherein said controller comprises a time controller configured to determine a time interval from said pulse generator delivering said pacing pulse to said first terminal to said pulse generator delivering said pacing pulse to said second terminal based on said audio signal.

4. The implantable medical device according to claim 1, wherein
said pulse generator is configured to generate a current pulse to be applied to a chamber of said heart by said quadropolar ventricular lead, said implantable medical device further comprising:
an impedance measuring circuit configured to determine a voltage signal resulting from said current pulse and determining an impedance signal based on said current pulse and said voltage signal; and
a time controller configured to determine a time interval from said pulse generator delivering said pacing pulse to said first terminal to said pulse generator delivering said pacing pulse to said second terminal based on said impedance signal.

5. The implantable medical device according to claim 1, wherein
said quadropolar ventricular lead is implantable in connection with a left ventricle of said heart and said lead connector further comprises another terminal electrically connectable to an electrode terminal of a right ventricular lead having a ventricular basal electrode electrically connected to said electrode terminal of said right ventricular lead; and
said controller is configured to control said pulse generator to deliver said pacing pulse to said first terminal and a pacing pulse to said another terminal followed by said pacing pulse to said second terminal during said cardiac cycle.

6. The implantable medical device according to claim 1, wherein
said quadropolar ventricular lead is implantable in connection with a left ventricle of said heart and said lead connector further comprises another terminal electrically connectable to an electrode terminal of a right ventricular lead having a ventricular apical electrode electrically connected to said electrode terminal of said right ventricular lead; and
said controller is configured to control said pulse generator to deliver said pacing pulse to said first terminal followed by said pacing pulse to said second terminal and a pacing pulse to said another terminal during said cardiac cycle.

7. The implantable medical device according to claim 1, wherein
said quadropolar ventricular lead is configured for implementation in connection with a left ventricle of said heart;
said lead connector further comprises another terminal electrically connectable to an electrode terminal of a right ventricular lead having a ventricular apical electrode electrically connected to said electrode terminal of said right ventricular lead; and
said controller is configured to control said pulse generator to deliver said pacing pulse to said first terminal, followed by said pacing pulse to said second terminal and a pacing pulse to said another terminal, followed by said pacing pulse to said third terminal and followed by said pacing pulse to said fourth terminal during said cardiac cycle.

8. The implantable medical device according to claim 1, wherein
said quadropolar ventricular lead is configured for implementation in connection with a left ventricle of said heart;
said lead connector further comprises another terminal electrically connectable to an electrode terminal of a right ventricular lead having a ventricular basal electrode electrically connected to said electrode terminal of said right ventricular lead; and
said controller is configured to control said pulse generator to deliver said pacing pulse to said first terminal and a pacing pulse to said another terminal, followed by said pacing pulse to said second terminal, followed by said pacing pulse to said third terminal and followed by said pacing pulse to said fourth terminal during said cardiac cycle.

9. A method of delivering cardiac therapy to a heart of a subject comprising:
generating pacing pulses;
delivering one of said pacing pulses to a basal portion of a ventricle of said heart;
delivering another of said pacing pulses to an apical portion of said ventricle after delivering said pacing pulse to said basal portion during a cardiac cycle; and
delivering another of said pacing pulses to a middle portion of said ventricle positioned in between said basal portion and said apical portion after delivering said pacing pulse to said apical portion during said cardiac cycle.

10. The method according to claim 9, wherein delivering said pacing pulse to said apical portion comprises delivering said pacing pulse to said apical portion of said ventricle after a time period of from 10 ms to 100 ms from delivering said pacing pulse to said basal portion during said cardiac cycle.

11. The method according to claim 9, further comprising:
recording an audio signal associated with a backward flow of blood out from said ventricle; and
determining a time interval from delivering said pacing pulse to said basal portion of said ventricle and delivering said pacing pulse to said apical portion of said ventricle based on said audio signal.

12. The method according to claim 9, further comprising:
delivering a current pulse to a chamber of said heart;
measuring a voltage signal resulting from said current pulse;
determining an impedance signal based on said current pulse and said voltage signal; and
determining a time interval from delivering said pacing pulse to said basal portion of said ventricle and delivering said pacing pulse to said apical portion of said ventricle based on said impedance signal.

13. The method according to claim 9, wherein delivering said pacing pulse to said basal portion comprises synchronously delivering said pacing pulse to a basal portion of a left ventricle of said heart and a basal portion of a right ventricle of said heart.

14. The method according to claim 9, wherein delivering said pacing pulse to said apical portion comprises synchronously delivering said pacing pulse to an apical portion of said left ventricle and an apical portion of a right ventricle of said heart.

15. The method according to claim 9, wherein delivering said pacing pulse to said middle portion comprises:
- delivering said pacing pulse to a first middle portion of said ventricle after delivering said pacing pulse to said apical portion during said cardiac cycle; and
- delivering said pacing pulse to a second middle portion of said ventricle positioned in between said first middle portion and said basal portion after delivering said pacing pulse to said first middle portion during said cardiac cycle.

* * * * *